United States Patent
Paran et al.

(10) Patent No.: US 8,642,845 B2
(45) Date of Patent: Feb. 4, 2014

(54) DISEASE RESISTANT PEPPER PLANTS

(75) Inventors: Ilan Paran, Karmey Yosef (IL); Serge Benarous, Kfar Achim (IL); Varda Ashkenazi, Yavne (IL)

(73) Assignees: Hazera Genetics Ltd, Berurim M.P., Shikmim (IL); The Agricultural Research Organization—Volcanic Center, Beit Dagan (IL)

( * ) Notice: Subject to any disclaimer, the term of this patent is extended or adjusted under 35 U.S.C. 154(b) by 270 days.

(21) Appl. No.: 12/866,154

(22) PCT Filed: Feb. 4, 2009

(86) PCT No.: PCT/IL2009/000129
§ 371 (c)(1),
(2), (4) Date: Aug. 4, 2010

(87) PCT Pub. No.: WO2009/098685
PCT Pub. Date: Aug. 13, 2009

(65) Prior Publication Data
US 2011/0035832 A1     Feb. 10, 2011

Related U.S. Application Data

(60) Provisional application No. 61/025,821, filed on Feb. 4, 2008.

(51) Int. Cl.
*A01H 1/00* (2006.01)
*A01H 5/00* (2006.01)
*A01H 5/10* (2006.01)
*C12N 15/00* (2006.01)
*C12N 15/82* (2006.01)

(52) U.S. Cl.
USPC ........ 800/317.1; 800/298; 800/278; 800/279; 800/265; 800/295; 435/6.1; 435/418

(58) Field of Classification Search
None
See application file for complete search history.

(56) References Cited

U.S. PATENT DOCUMENTS

2005/0124010 A1    6/2005   Short et al.

FOREIGN PATENT DOCUMENTS

WO       2004057941  A2     7/2004

OTHER PUBLICATIONS

Caranta et al., Development of a CAPS marker for the Pvr4 locus: A tool for pyramiding potyvirus resistance genes in pepper, Genome, 1999, pp. 1111-1116, vol. 42, National Research Council, Canada.
Lefebvre, Molecular Markers for Genetics and Breeding: Development and Use in Pepper (*Capsicum* spp.), Biotechnology in Agriculture and Forestry: Molecular Marker Systems in Plant Breeding and Crop Improvement, 2004, pp. 189-214, vol. 55, Springer-Verlag, Berlin Heidelberg.
Lefebvre et al., QTLs for resistance to powdery mildew in pepper under natural and artificial infections, Theoretical and Applied Genetics, 2003, pp. 661-666, vol. 107, Springer-Verlag, Berlin Heidelberg.
Yeam et al., Allele-specific CAPS markers based on point mutations in resistance alleles at the pvr1 locus encoding eIF4E in *Capsicum*, Theoretical and Applied Genetics, 2005, pp. 178-186, vol. 112, Springer-Verlag, Berlin Heidelberg.
Cavatorta et al., Positive Darwinian Selection at Single Amino Acid Sites Conferring plant Virus Resistance, Journal of Molecular Evolution, 2008, pp. 551-559, vol. 67, No. 5, Springer Science+Business Media LLC.
International Search Report dated Aug. 21, 2009 in corresponding International Application No. PCT/IL2009/000129.

*Primary Examiner* — Medina A Ibrahim
(74) *Attorney, Agent, or Firm* — Cooley LLP

(57) ABSTRACT

The present invention relates to pepper plants resistant to powdery mildew disease as well as to infection by potyviruses, particularly potato virus Y (PVY). Specifically, the present invention relates to pepper plants comprising a viral resistance allele and a powdery mildew resistant allele in cis configuration on the same chromosome, such that the two resistance alleles are in coupling phase.

18 Claims, 3 Drawing Sheets

Figure 1:
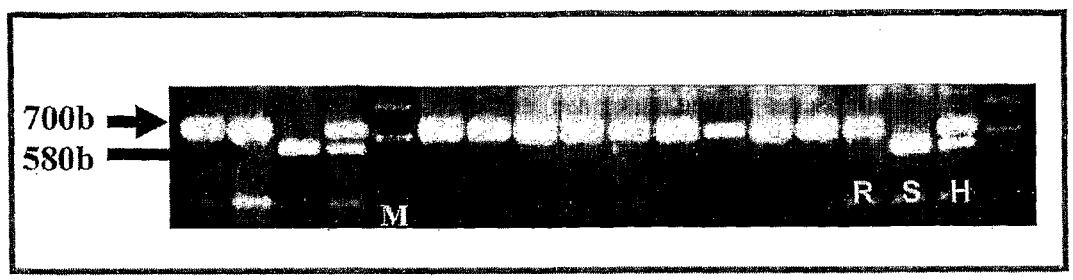

TGAGGCAGATGATGAAGTTGAAGAAGGTGAAATTGTTGAAGAAACTG
ATGATACGACGTCGTATTTGAGCAAAGAAATAGCAACAAAGCATCCA
TTAGAGCATTCATGGACTTTCTGGTTTGATAATCCAGTGGCGAAATCG
AGACAAGCTGCTTGGGGTAGCTCGCTTCGCAACGTCTACACTTTCTCC
ACTGTTGAAGATTTTGGGGTGCTTGTAAATTTTTTTAATTTAATTTA
ATTTTTTATTTTATTGCTTTTTTTTTTTGTTTAATAAATTGGGTATTAG
GGGAATCGAACAATCACGAACAAGGTGGAAGTTTAGGTAGCCAATTA
ACTGAGTTATTGCGATTTTATTTTAGTTAAGTTTTTTTAAGGCGTAA
TATATAAATGTGCACTTTAATATACCCTTGAACTTGTATAAAGTTGAAC
AGGTAGACACATGTTCCTTATGTAGTGTCCTACAGGTATTATGACGCA
TTGGGACGTTGTGTCTGCTTGTGCACGTCCAAAGTTGGTCATAAATGC
GAATTGATGCCAAGTTAAAGGGCCATGTTTATGTATTATGCGTTTTTT
TAAGCTTATTATAGGGGAATGGNAAATGGGGAGGAATTGCAAGGTGA
GGAATCGACCCTTCATGANCAAGGTAAAAGTTGAGGTAGATAATCAA
TTGAGCTACTAAGATTCTCGGGGTATATTTATGGTTG

FIG. 3

DISEASE RESISTANT PEPPER PLANTS

CROSS-REFERENCE TO RELATED APPLICATIONS

This application is a national stage of International Patent Application No. PCT/IL2009/000129, filed Feb. 4, 2009, which claims the benefit of U.S. Provisional Application Ser. No. 61/025,821, filed Feb. 4, 2008, each of the International Patent Application No. PCT/IL2009/000129 and the U.S. Provisional Application Ser. No. 61/025,821 is hereby incorporated by reference in its entirety for all purposes.

FIELD OF THE INVENTION

The present invention relates to pepper plants resistant to powdery mildew disease as well as to infection by potyviruses, particularly potato virus Y (PVY). Specifically, the present invention relates to pepper plants comprising a viral resistance allele and a powdery mildew resistant allele in cis configuration on the same chromosome, such that the two resistance alleles are in coupling phase.

BACKGROUND OF THE INVENTION

Powdery mildew is a plant disease caused by fungal parasite pathogens. Powdery mildew caused by the fungus *Leveillula taurica* is one of the most important diseases in pepper, mainly in sweet pepper, and it also affects other vegetable crops. Since the early 1990s this pathogen is reported to cause epidemics in greenhouses and in open fields, in most of the pepper production areas. Whereas most of the fungi species causing powdery mildew are ectoparasites, the mycelium of *L. taurica* grows intercellularly within the host tissues, limiting the efficiency of chemical fungicides. One of the most pronounced symptoms of the disease caused by this parasite is premature leaf shading, which strongly affects fruit production and quality, rendering significant portion of the fruit unmarketable.

Various resistance sources to powdery mildew were found under natural infection conditions in different pepper (*Capsicum*) species, including *Capsicum annuum*, *C. baccatum* and *C. chinense*. Quantitative genetic analyses have shown that three to five genetic factors with significant epistatic effects are involved in the resistant phenotype under severe infection conditions (Daubèze et al., 1995. Plant Breed. 114: 327-332; Murphy and Deshpande, 1997. Vegetable Sci. 24:127-131). Recently, seven genomic regions including additive quantitative trait locus (QTL) and epistatic interactions were detected in the highly powdery mildew resistant *C. annuum* genitor H3, which has small, pungent fruit. These findings, i.e., the complex inheritance pattern of resistance together with the observation that powdery mildew epidemic is highly dependent on environmental conditions, explain the high variability found in the response of pepper plants to the pathogen (Lefebvre et al., 2003. Theor. Appl. Genet. 107:661-666).

U.S. Pat. No. 6,350,933 discloses nucleic acids and proteins which confer powdery mildew disease resistance. The nucleic acids can be used to produce transgenic plants of various types that are resistant to pests. Antibodies to proteins disclosed in the invention are also provided.

U.S. Pat. No. 6,677,510 discloses plants resistant to powdery mildew, specifically dogwood (*Cornus florida*) cultivars that are resistant to infestation with powdery mildew fungi, and materials and methods for identifying, characterizing, and/or producing powdery mildew resistant plants. It also discloses polynucleotide sequences, and patterns of polynucleotide sequences, which are associated with resistance to powdery mildew, useful in identifying and characterizing plants having resistance to powdery mildew. However, these means and methods are mainly directed to ornamental plants.

Plant viruses are a continuing problem in the agricultural industry. Viral infection in plants causes a variety of undesirable effects including stunted growth, altered morphology, reduced yield, diminished quality and increased susceptibility to damage by other pests. Attempts to control or prevent infection of a crop by a plant virus have been made, yet viral pathogens continue to be a significant problem in agriculture.

Potyviruses comprise about 30% of all known plant viruses, and viruses belonging to this group cause significant damage to agricultural crops. The family Potyviridae is characterized by a single-stranded sense RNA genome with a covalently bound viral-encoded protein (VPg) attached to the 5' terminus, and a 3' poly-A tract. The genome is approximately 10 kb in length and is translated as a polyprotein that is subsequently cleaved into smaller polypeptides by viral-encoded proteases. Potato virus Y (hereinafter PVY) is a member of the potyvirus plant virus group. PVY is a positive-sense, single-stranded RNA virus that is surrounded by a repeating proteinaceous monomer, which is termed the coat protein (CP). The encapsidated virus has flexous rod morphology, which is characteristic of the potyvirus group. The majority of the potyviruses, including PVY, are transmitted in a non-persistent manner by aphids. The host range of PVY includes potato, tobacco, tomato and pepper, and the ease of its transmittance by aphids results in a significant damage to these crops and to a drastic reduction in their economic value.

Potyvirus infection requires the interaction of host factors with viral proteins and RNA for viral replication and systemic spread. The "negative model" of plant virus resistance predicts that a recessive resistance gene may represent a deleted or defective host protein that is essential for viral infection but is not necessary for the normal function of the plant cell. Recessive resistance is especially prevalent for potyviruses, comprising approximately 40% of all known resistance genes. Several host genes whose mutations impair the infection cycle of plant viruses have been characterized, particularly in *Arabidopsis* (Kang et al. Annu. Rev. Phytopathol. 43:581-621). The gene encoding the translation initiation factor eIF4E has been identified repeatedly in diverse hosts as a naturally occurring recessively inherited resistance locus. Mutations in this gene have been shown to produce resistance to potyviruses in several plant species including pepper. The mutations occur at the pvr1 locus, recently shown to be identical to the pvr2 locus (Ruffel et al., 2002. The Plant J. 32:1067-1075; Kang et al., 2005. The Plant J. 42:392-405).

Many of the genes involved in virus resistance, including the virus resistance gene pvr1 identified in *Capsicum*, have been used successfully as effective and stable markers for identifying sources of resistance in crop breeding programs. Yearn et al. (2005. Theor. Appl. Genet. 112:178-186) reported the generation and use of molecular markers that define loci for selection of potyvirus-resistance *Capsicum* plants, using cleaved amplified polymorphic sequences (CAPS). Such CAPS markers were developed for three recessive viral resistance alleles, pvr1, pvr1[1] and pvr1[2].

Alternatively, attempts are directed towards the use of genetic engineering techniques to produce virus resistance plants (for example, U.S. Pat. Nos. 5,589,612; 5,939,603; 5,986,175; and 6,806,400).

As of today, pepper plants resistant to potyviruses, including varieties suitable for commercial crop growth are available. Nevertheless, chemical control is still widely used to combat viral infection.

In recent decades, awareness of the harmful effect of extensive use of pesticides on the environment has been constantly grown. Efforts are directed at the development of sustainable agriculture, including maintaining high yield crop production with significant reduction in employing environmentally hazardous chemicals.

Chemical control of the fungus *L. taurica*, causing powdery mildew disease in pepper cultivars, involves high costs and is hazardous to the environment.

Thus, there is a great demand for, and it would be highly advantages to have pepper plants, suitable for growth on a commercial scale, which are resistant to more than one pathogen.

SUMMARY OF THE INVENTION

The present invention relates to pepper (*Capsicum*) plants resistant to powdery mildew caused by the fungus *Leveillula taurica* as well as to infection by at least one potyvirus, particularly potato virus Y (PVY), wherein the resistance to both pathogens is in coupling phase.

According to one aspect, the present invention provides a pepper plant comprising within its genome at least one potyvirus resistance allele and at least one powdery mildew (PM) resistance allele, wherein the resistance alleles are present in cis configuration on the same chromosome, such that said two resistance alleles are in coupling phase.

The present invention is based in part on the discovery that pepper plants which are resistant to powdery mildew are susceptible to infection by PVY, and vice versa. This phenomenon results from a tight linkage between the PVY resistance-related pvr1 gene and a powdery mildew resistance-related gene. The present invention now shows that the pvr1 resistance allele is located on the same chromosome as the powdery mildew susceptible allele. The present invention is further based on the identification of recombination events in the region of these tightly-linked genes, which lead to the coupling of both resistance alleles in a cis configuration on the same chromosome.

According to one embodiment, the at least one potyvirus resistance allele and the at least one PM resistance allele are located on chromosome 4.

According to certain embodiments, the pepper plant is substantially resistant to PM disease caused by the fungus *L. taurica*. According to currently preferred embodiments, the pepper plant is resistant to PM disease caused by the fungus *L. taurica* as well as to infection by at least one potyvirus. According to one embodiment, the potyvirus is selected from the group consisting of potato virus Y (PVY); potato virus A (PVA); tobacco etch virus (TEV); and pepper mottle virus (PepMoV). According to certain currently preferred embodiments, the potyvirus is PVY.

As used herein, the term "substantially resistant" with regards to powdery mildew refers to plants that, upon inoculation, does not show, or show only mild symptoms of the disease. The disease symptoms include chlorotic spots on the upper leaf surface and a white powder-like sporulation on the corresponding area of the lower leaf surface.

With regard to PVY, the term "substantially resistant" refers to plants that upon inoculation with the virus, does not show, or show only mild symptoms of the disease. Symptoms of the disease are shown as green spots on the leaves, creating a "mosaic like" pattern.

According to other embodiments, the pepper plant is suitable for commercial growth and has edible sweet fruit.

According to further embodiments, the pepper plant comprises within its genome a DNA sequence which couples with resistance to a potyvirus, and a DNA sequence which couples with susceptibility to potyvirus, wherein said pepper plant is resistant to powdery mildew. According to one embodiment, the DNA sequence coupling with resistance or susceptibility to potyvirus is located within the pvr1 gene (NCBI Accession No. AY485129; Kang et al., 2005. Plant J. 42:392-405). According to another embodiment, the potyvirus is PVY.

According to yet another embodiment, the DNA sequence coupling with potyvirus resistance comprises a polynucleotide sequence as set forth in SEQ ID NO: 1. According to one currently preferred embodiment, the DNA sequence coupling with potyvirus resistance is a template for amplification of a DNA fragment using a first primer having a polynucleotide sequence as set forth in SEQ ID NO:2 and a second primer having a polynucleotide sequence as set forth in SEQ ID NO:3. The resulting DNA fragment lacks a restriction site for the restriction enzyme BseNI.

According to a further embodiment, the DNA sequence coupling with potyvirus susceptibility is a template for amplification of a DNA fragment using a first primer having a polynucleotide sequence as set forth in SEQ ID NO:2 and a second primer having a polynucleotide sequence as set forth in SEQ ID NO:3. The resulting DNA fragment contains a restriction site for the restriction enzyme BseNI.

The plants of the invention are preferably non-genetically modified (non-GMO); however it is to be understood that the addition or deletion of traits by transformation is explicitly encompassed within the scope of the invention.

Pollen and ovules from the pepper plants of the present invention; the seeds produced from same and the plants grown from the seeds and fruit produced by these plants, are also encompassed within the scope of the present invention.

The pepper plants of the present invention advantageously can further comprise beneficial agronomical traits as are well known in the art, including but not limited to high germination rate, herbicide resistance, insect resistance, resistance to at least one disease, resistance to various types of non-biotic stress, male sterility and vigorous growth.

According to one embodiment, the plants or progeny or parts thereof have been transformed to include the at least one additional trait so that its genetic material contains one or more transgenes operably linked to one or more regulatory elements. Pepper plants and parts thereof produced from the transformed varieties are also encompassed within the scope of the present invention.

The pepper plants of the present invention can be genetically stable inbred lines as well as hybrids produced by crossing two different strains. As used herein, "parent lines" refers to open pollinated, inbred lines, stable for the desired traits over cycles of self-pollination and planting. According to certain embodiments, the pepper plants of the present invention are capable of producing a crop of a commercial value.

According to certain embodiments, the pepper plants having dual resistance according to teachings of the present invention are homozygous for the potyvirus resistance allele and for the PM resistance allele.

According to other certain embodiments, the pepper plants having dual resistance according to teachings of the present invention are homozygous for the potyvirus resistance allele and heterozygous for the PM resistance allele.

According to yet another aspect, the present invention provides a tissue culture regenerated from the plants of the present invention and plants regenerated therefrom.

According to one embodiment, the tissue culture comprises cells or protoplasts derived from a tissue selected from the group consisting of, but not limited to, leaves, pollen, embryos, roots, root tips, anthers, flowers, fruit and seeds.

According to another embodiment, a plant regenerated from the tissue culture comprise within its genome at least one potyvirus resistance allele and at least one powdery mildew (PM) resistance allele, present in cis position on the same chromosome such that the two resistance alleles are in coupling phase.

According to another aspect, the present invention provides pepper seeds wherein plants grown from the seeds comprise within their genome at least one potyvirus resistance allele and at least one powdery mildew (PM) resistance allele, wherein the resistance alleles are present in cis configuration on the same chromosome, such that the two resistance alleles are in coupling phase.

According to another aspect, the present invention provides pepper seeds, wherein the at least one potyvirus resistance allele and the at least one PM resistance allele are located on chromosome 4.

According to another aspect, the present invention provides pepper seeds, wherein the plant grown from the seed is substantially resistant to PM disease caused by the fungus $L.$ $taurica$.

According to another aspect, the present invention provides pepper seeds, wherein the plant grown from the seed is further resistant to infection by at least one potyvirus.

According to another aspect, the present invention provides pepper seeds, wherein the potyvirus is selected from the group consisting of potato virus Y (PVY), potato virus A (PVA), tobacco etch virus (TEV) and pepper mottle virus (PepMoV).

According to another aspect, the present invention provides pepper seeds, wherein the potyvirus is PVY.

According to another aspect, the present invention provides pepper seeds, wherein inoculation of the plant grown from said seed with $L. taurica$ results in minor appearance or no appearance of powdery mildew disease symptoms on the leaves of said plant.

According to another aspect, the present invention provides pepper seeds, wherein said symptoms include chlorotic spots on the upper leaf surface and white powder-like sporulation on the corresponding area of the lower leaf surface.

According to another aspect, the present invention provides pepper seeds, wherein inoculation of the plant grown from said seed with PVY results in minor or no appearance of mosaic like green spots on the leaves of said plant.

According to another aspect, the present invention provides pepper seeds, comprising within its genome a DNA sequence which couples with resistance to a potyvirus, and a DNA sequence which couples with susceptibility to potyvirus, wherein said pepper plant is resistant to powdery mildew.

According to another aspect, the present invention provides pepper seeds, wherein the DNA sequence coupling with potyvirus resistance is a template for amplification of a DNA fragment using a first primer having a polynucleotide sequence as set forth in SEQ ID NO:2 and a second primer having a polynucleotide sequence as set forth in. SEQ ID NO:3, said DNA fragment lacking a restriction site for the restriction enzyme BseNI.

According to another aspect, the present invention provides pepper seeds, wherein the DNA sequence coupling with potyvirus susceptibility is a template for amplification of a DNA fragment using a first primer having a polynucleotide sequence as set forth in SEQ ID NO:2 and a second primer having a polynucleotide sequence as set forth in SEQ ID NO:3, said DNA fragment containing a restriction site for the restriction enzyme BseNI.

According to another aspect, the present invention provides a pepper plant, or a part thereof, produced by growing the seed as detailed above.

According to yet a further aspect, the present invention provides a fruit of a pepper plant comprising within its genome at least one potyvirus resistance allele and at least one powdery mildew (PM) resistance allele, present in cis configuration on the same chromosome such that the two resistance alleles are in coupling phase, wherein the fruit are edible sweet fruit. According to certain currently preferred embodiments, the potyvirus is PVY.

According to an additional aspect, the present invention provides a method of producing a pepper plant comprising within its genome at least one potyvirus resistance allele and at least one powdery mildew (PM) resistance allele wherein the alleles are present in cis configuration on the same chromosome, comprising the steps of:

a) providing a first pepper plant resistant to infection by $L. taurica$ and susceptible to potato virus Y (PVY) and a second pepper plant susceptible to infection by $L. taurica$ and resistant to PVY;

b) crossing the first and the second pepper plants of step (a) to produce an $F_1$ pepper plant progeny;

c) selfing the $F_1$ pepper plant of step (b) to produce an $F_2$ pepper plant progeny;

d) analyzing the progeny of step (c) for plants resistant to infection with $L. taurica$ comprising within their genome a PVY resistant allele and a PVY susceptibility allele; and e) selecting at least one plant having the characteristics of step (d), comprising within its genome at least one potyvirus resistance allele and at least one powdery mildew (PM) resistance allele wherein the alleles are present in cis position on the same chromosome.

According to certain embodiments, the method further comprises selfing the plant of step (e) to obtain a progeny homozygous for the potyvirus resistance allele and the PM resistance allele.

According to further certain embodiments, the method as detailed above further comprises the steps of:

a) isolating a genomic DNA sample from the plant;

b) amplifying a DNA segment using a first primer having a polynucleotide sequence as set forth in SEQ ID NO:2 and a second primer having a polynucleotide sequence as set forth in SEQ ID NO:3; and, c) subjecting the amplified DNA segment to restriction with the restriction enzyme BseNI;

wherein the absence of a BseNI restriction site within said amplified DNA segment characterizes the plant as resistant to infection by potyvirus and the presence of the BseNI site characterizes the plant as susceptible to infection by potyvirus.

It is now disclosed that surprisingly, resistance to potyvirus infection in pepper plants is in repulsion phase to resistance to powdery mildew disease in nature.

Thus, according to a further aspect, the present invention provides a method for characterizing a pepper plant as resistant or susceptible to infection by $L. taurica$, comprising the steps of:

a) isolating a genomic DNA sample from the plant;

b) amplifying a DNA segment using a first primer having a polynucleotide sequence as set forth in SEQ ID NO:2 and a second primer having a polynucleotide sequence as set forth in SEQ ID NO:3; and c) subjecting the amplified DNA segment to restriction with the restriction enzyme BseNI;

wherein the presence of BseNI restriction site within said amplified DNA segment characterizes the plant as resistant to infection by *L. taurica* and the absence of the BseNI site characterizes the plant as susceptible to infection by *L. taurica*.

Other objects, features and advantages of the present invention will become clear from the following description and drawings.

BRIEF DESCRIPTION OF THE FIGURES

In order to understand the invention and to see how it may be implemented in practice, a plurality of preferred embodiments will now be described, by way of non-limiting example only, with reference to the accompanying Figures, wherein:

FIG. 1 is a photographic representation of the lower leaf surface of leaves obtained from resistant pepper plants and from susceptible plants as preferred embodiments of the invention;

FIG. 2 is a photographic representation of the segregation of the pvr gene in F2 plants, using the DNA markers as described herein. R—Resistant plant homozygote to pvr; S—Susceptible plant homozygote to pvr; H—partially resistant plant hetrozygote to pvr; M—pPBR322 DNA/Alu Marker; and, FIG. 3 is a schematic presentation of SEQ ID NO:1, which is the nucleotide sequence of a DNA fragment amplified by SEQ ID NO:2 and SEQ ID NO:3 primers of the present invention, using the pvr gene as a template.

DETAILED DESCRIPTION OF THE INVENTION

Definitions

As used herein, the term "pepper plant" refers to a plant of the genus *Capsicum*, specifically to plants of *Capsicum annuum.*

As used herein, the term "powdery mildew" refers to a disease caused by the fungus *Leveillula taurica*. Plants infected with the fungus will display white powder-like spots on the leaves. The lower leaves are the most affected, and as the disease progresses, the mildew spread up to the upper leaves. Disease progression is also associated with the spots getting larger and thicker due to a massive numbers of spores formed. Leaves infected with the fungus are often shed from the plant, exposing the fruit to sunlight that may damage the fruit As used herein the term "potyvirus" refers to a virus infecting plants that belong to the family Potyviridae. Members of the Potyviridae family include: potato virus Y (PVY), potato virus A (PVA), tobacco etch virus (TEV) and pepper mottle virus (PepMoV). The term PVY refers to potato virus Y, belonging to the potyvirus plant virus group. PVY is a positive-sense, single-stranded RNA virus that is surrounded by a repeating proteinaceous monomer, which is termed the coat protein (CP). The encapsidated virus has flexous rod morphology, which is characteristic of the potyvirus group. The majority of the potyviruses are transmitted in a non-persistent manner by aphids.

As used herein, the term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus.

As used herein, the term "locus" (loci plural) means a specific place or places or a site on a chromosome where for example a gene or genetic marker is found.

As used herein, the terms "in cis" refer to a genetic condition in which the alleles of two different loci occur together linked on one (homologous) chromosome. For example, when the PVY-resistance allele and PM-resistance allele are located on one chromosome homologue, these alleles are "in cis". In contrast, if the PVY-resistance allele and PM-resistance allele are located on different homologous chromosomes of a homologous pair, they are said to be in "trans".

A "recombination" or "recombination event" as used herein refers to a chromosomal crossing over or independent assortment. The term "recombinant" refers to a plant having a new genetic make up arising as a result of recombination event.

As used herein, dominant alleles of linked genes are present in the same chromosome, and are referred to as "coupling phase". In contrast, in "repulsion phase" linkage, the dominant allele of one gene is present with the recessive allele of the other gene in the same chromosome.

As used herein, the term coupling is analagous to co inheriting or co segregating in some of the embodiments of the invention.

As used herein, the terms "potyvirus resistance allele" or "PVY-resistance allele" refer to an allele, which when present in the genome, confers resistance or partial resistance to a potyvirus or to potato virus Y, respectively, on a pepper plant. According to certain embodiments of the invention, the "potyvirus resistance allele" is the pvr1 gene resistance allele (also known as pvr2). The term "pvr gene" as used herein refers to NCBI Accession No. AY485129; Kang et al., 2005 Plant J. 42:392-405. A plant or plants are "resistant" when no symptoms or only mild symptoms of the disease (i.e., only few mosaic like green spots) appear after deliberate infection of the plant with the virus. Resistant plants are homozygous for the pvr allele.

The term "PM-resistance allele" as used herein refers to an allele, which when present in the genome, confers resistance or partial resistance to powdery mildew caused by the fungus *L. taurica*. The pepper plant or plants resistant to *L. taurica* are characterized as heterozygous or homozygous for the PM-resistance allele. Phenotypically, heterozygous resistant plants show only minor disease symptoms and homozygous resistant plant do not show the typical symptoms of chlorotic spots on the upper leaf surface and the white powder-like sporulation on the corresponding area of the lower leaf surface.

As used herein, the term "trait" refers to characteristic or phenotype. For example, in the context of the present invention "resistance" and "susceptibility" relates to the symptoms observed on a plant infected with the fungus *L. taurica* or with a potyvirus as described herein. A trait may be inherited in a dominant or recessive manner, or in a partial or incomplete-dominant manner. A trait may be monogenic (i.e. determined by a single locus) or polygenic (i.e. determined by more than one locus) or may also result from the interaction of one or more genes with the environment. A dominant trait results in a complete phenotypic manifestation at heterozygous or homozygous state; a recessive trait manifests itself only when present at homozygous state.

As used herein, the term "homozygous" means a genetic condition existing when two identical alleles reside at a specific locus, but are positioned individually on corresponding pairs of homologous chromosomes in the cell of a diploid organism. Conversely, as used herein, the term "heterozygous" means a genetic condition existing when two different alleles reside at a specific locus, but are positioned individually on corresponding pairs of homologous chromosomes in the cell of a diploid organism.

As used herein, the term "plant" includes the whole plant or any parts or derivatives thereof, such as plant cells, plant protoplasts, plant cell tissue cultures from which pepper plants can be regenerated, plant calli, embryos, pollen, ovules, fruit (e.g. harvested pepper), flowers, leaves, seeds, roots, root tips and the like.

Seeds of the pepper plant comprising within its genome at least one potyvirus resistance allele and at least one powdery mildew (PM) resistance allele, wherein said resistance alleles are present in cis configuration on the same chromosome, such that said two resistance alleles are in coupling phase are obtainable with regard to a deposit made under the Budapest treaty regulations. These genomes can be obtained from said deposited material but can also be obtained from other material. The sequence of the genes obtained from other material may vary from the sequence of the gene in the deposited material ("variant"). Deposit Number NCIMB or a genetic variant thereof, which refers essentially the same phenotype are available. Seeds of pepper plants similar to the above, further comprising at least one additional trait selected from the group consisting of high germination rate, herbicide resistance, insect resistance, resistance to at least one disease, resistance to various types of non-biotic stress, male sterility and vigorous growth are obtainable with regard to a deposit made under the Budapest treaty regulations. These genomes can be obtained from said deposited material but can also be obtained from other material. The sequence of the genes obtained from other material may vary from the sequence of the gene in the deposited material ("variant"). Deposit Number NCIMB or a genetic variant thereof, which refers essentially the same phenotype are available.

Plants of the Invention and Parts Thereof

The present invention relates to pepper plants which are resistant to powdery mildew and to infection by a potyvirus, particularly potato virus Y, each of which is known to have deleterious effects on pepper plant growth, resulting in reduced crop yield and significant economic loss.

The present invention discloses for the first time that the allele for resistance to powdery mildew is linked to the allele for susceptibility to potato virus Y (PVY), wherein both alleles are located on chromosome 4 in the genome of pepper plants. According to one aspect, the present invention provides a pepper plant comprising within its genome at least one potyvirus resistance allele and at least one powdery mildew (PM) resistance allele, wherein the resistance alleles are present in cis configuration on the same chromosome, such that said two resistance alleles are in coupling phase.

The plants of the present invention originate from pepper plants resistant to PM and susceptible to potyvirus and pepper plants susceptible to PM and resistant to potyvirus, crossed to generate a population from which recombinant plants, comprising both resistance alleles on the same chromosome in cis, are selected. The parent plants for producing the plants of the present invention were selected from a germplasm collection of proprietary breeding material belonging to Hazera Genetics Ltd. (Israel), and breeding material provided by The Horticultural Research Organization, Volcani Center (Israel). Selection for plants resistant to PM or to a potyvirus was based on plant infection and disease severity assessment as well as on molecular assays.

Phenotypic resistance to PM was based on infection of the plant with the fungus L. taurica. The severity of disease symptoms depends not only on the genetic background but also on the plant age and environmental conditions. Thus, disease symptoms were measured at replicates at a specific developmental time point. Plants that did not develop any symptoms were designated as "resistant". High occurrence of fungus on the plant defined the plant as susceptible and "moderately resistant plants" where those plants showing a low level of fungal occurrence.

Thus, according to certain embodiments of the present invention, inoculation with L. taurica results in minor appearance or no appearance of powdery mildew disease symptoms on the leaves of the pepper plant.

Phenotypic resistance to the potyvirus PVY was confirmed when the typical mosaic-like green spot were not detected on the leave of the infected plant. Thus, according to the present invention, inoculation with PVY results in minor or no appearance of mosaic like green spots on the leaves of the pepper plant.

Molecular assays using molecular markers were also used to discriminate between the presence and absence of the PM and PVY resistance alleles. These markers can be further used in marker-assisted selection, i.e. in determining the allelic makeup of the plant at the PM-resistance related locus and at the potyvirus-resistant related locus, and the selection of plants having the desired resistant allele in a cis configuration on the same chromosome.

Resistance to potyvirus was confirmed by analysis of DNA extracted from candidate plants for the presence of the pvr1 resistance allele. Any method known in the art can be used to identify the presence of the pvr1 resistance allele or parts thereof within the DNA sample.

According to certain embodiments, the presence of the pvr1 resistance allele was confirmed by amplification of a DNA segment using a set of primers and subjecting the resulted DNA segment to restriction by restriction enzymes. According to certain currently preferred embodiments, the DNA segment was amplified using a first primer having a polynucleotide sequence as set forth in SEQ ID NO:2 and a second primer having a polynucleotide sequence as set forth in SEQ ID NO:3, and the resulted DNA segment was subjected to restriction by the restriction enzyme BseNI. The absence of BseNI restriction site within the amplified DNA segment of about 700 bp, having the sequence as set forth in SEQ ID NO:1 (FIG. 3), is indicative of the presence of pvr1 resistance allele.

The presence of BseNI restriction site within the amplified DNA segment is indicative of the presence of pvr1 susceptibility allele. Two segments are obtained after restriction with BseNI, one of about 130 bp and one of about 580 bp.

Resistance to PM was confirmed by analysis of DNA extracted from candidate plants for the presence of the pvr1 susceptibility allele, as described hereinabove. It is to be understood that similar assays can be developed for identifying the PM and potyvirus resistance/susceptibility alleles, using routine molecular biology techniques as are known to a person skilled in the art. For example, other fragments of the pvr1 gene or the adjacent PM-resistant related gene may be used to design PCR primer pairs or probes for nucleic acid hybridization and to develop discriminating molecular assays based on the nucleic acid information of the region amplified by such primer pairs or of the nucleic acid sequence to which such probes hybridize. The exact type of assay developed is not important, as long as it can discriminate between PM resistant allele and potyvirus resistance allele and homozygosity/heterozygosity at the desired locus.

In order to perform the marker-assisted selection in the methods of the present invention, the subject pepper plants or plant parts are, for example, first subjected to DNA extraction, as described in the Example section herein below or by other techniques as are known in the art. Once the extraction is complete, a molecular assay can be performed, including, but not limited to, a cleaved amplified polymorphic sequence (CAPS) assay (see for example, Akopyanz et al., 1992. Nucleic Acid Research 20:6221-6225; Konieczny and Ausubel, 1993. The Plant J. 4:403-410) or a Sequence Characterized Amplified Region (SCAR) assay. A SCAR assay involves amplifying DNA at the locus (e.g. the PVY—resistance locus) by PCR followed by digestion with restriction enzymes. Polymorphisms between the nucleic acid sequences differentiates between different alleles (such as, but not limited to, the pvr1 resistance and susceptibility alleles) by resulting for example in different sized restriction fragments.

The CAPS markers were used for indirect selection of potyvirus resistance in *Capsicum* based on genomic sequence, according to Yeam et al., 2005 and Ruffel et al., 2002, both references being incorporated herein in their entirety.

Examination of the segregation of F2 pepper plants resulting from a cross between an inbred line resistant to PM and susceptible to PVY with an inbred line resistant to PVY and susceptible to PM showed that the pvr1 gene and the PM-resistance related gene are located on chromosome 4, about 2cM apart from each other. Because resistance to PM is in trans configuration with resistance to PVY (the resistant allele to PM is on the same chromosome with the susceptible allele to PVY), plants that are resistant to both PM and PVY are the result of recombination events between the two resistant genes.

According to certain embodiments, the pepper plants of the present invention are substantially resistant to infection by potyvirus, particularly PVY, as well as to infection by *L. taurica*. Maximal resistance to potyviruses is obtained when the plants are homozygous to the pvr1 resistant allele. This observation is in line with previous results postulating that pvr1-mediated resistance of pepper (*Capsicum* sp.) to potato virus Y (PVY) is recessive (Ruffle et al., 2002. supra). Pepper plants showing moderate symptoms of powdery mildew were typically heterozygous to the PM-resistance allele, while resistant plants were homozygous to this allele. Thus, since both traits are located on the same chromosome, according to certain embodiments, plants comprising the pvr1 resistant allele and the PM resistant allele in cis configuration are homozygous.

The development of a commercial, superior pepper strain requires a significant breeding effort. Pepper plants resistant to potyviruses and/or to PM, that may be used as a source for generating the plants of the present invention, are not necessarily useful for commercial scale production, as they may have undesirable traits such as poor germination rate, low vigor, low fruit yield, small fruit, susceptibility to other diseases, etc. Such undesirable traits, also known as "genetic drag symptoms" will adversely affect the commercial acceptance of inbred or hybrid plant line by growers. Generally, the presence of an adverse level of genetic drag can be determined by the presence of one or more of these symptoms to such a degree that the plant line becomes commercially unacceptable.

The present invention encompasses any part of the plants of the present invention, comprising within their genome at least one potyvirus resistance allele and at least one PM resistance allele in cis configuration such that the two resistance alleles are in coupling phase, including pollen, ovules and tissue cultures regenerated from these plants. Pollen and ovules are used in breeding programs, in general and as described by the present invention. Tissue culture of pepper can be used for the in vitro regeneration of a pepper plant as is well known in the art.

Plants comprising within their pedigree a pepper plant having in its genome at least one potyvirus resistance allele and at least one PM resistance allele in cis configuration on the same chromosome, are also encompassed within the scope of the present invention.

According to one embodiment of the present invention, the pepper plant is homozygous for the potyvirus resistance allele and for the PM resistance allele.

According to a further embodiment of the present invention, the plant is homozygous for the potyvirus resistance allele and heterozygous for the PM resistance allele.

According to a further embodiment of the present invention the pepper plant is selected from the group consisting of an inbred line and a hybrid.

According to a further embodiment of the present invention, the pepper plant of claim 1, further comprising at least one additional trait selected from the group consisting of high germination rate, herbicide resistance, insect resistance, resistance to at least one disease, resistance to various types of non-biotic stress, male sterility and vigorous growth.

According to a further embodiment of the present invention, the aforementioned additional trait is introduced by a method selected from the group consisting of breeding, single trait conversion and transformation.

According to other embodiments, the present invention provides seeds of pepper wherein the plants grown from the seeds comprise within their genome at least one potyvirus resistance allele and at least one PM resistance allele in cis configuration on the same chromosome, such that the two resistance alleles are stably in coupling phase.

Thus according to further embodiments, the present invention provides seeds as defined above, wherein the at least one potyvirus resistance allele and the at least one PM resistance allele are located on chromosome 4.

According to further embodiments, the present invention provides seeds as defined above, wherein the plant grown from the seed is substantially resistant to PM disease caused by the fungus *L. taurica*.

According to further embodiments, the present invention provides seeds as defined above, wherein the plant grown from the seed is further resistant to infection by at least one potyvirus.

According to further embodiments, the present invention provides seeds as defined above, wherein the potyvirus is selected from the group consisting of potato virus Y (PVY), potato virus A (PVA), tobacco etch virus (TEV) and pepper mottle virus (PepMoV).

According to further embodiments, the present invention provides seeds as defined above, wherein the potyvirus is PVY.

According to other embodiments, the present invention provides seeds as defined above, wherein inoculation of the plant grown from said seed with *L. taurica* results in minor appearance or no appearance of powdery mildew disease symptoms on the leaves of said plant.

According to other embodiments, the present invention provides seeds as defined above, wherein said symptoms include chlorotic spots on the upper leaf surface and white powder-like sporulation on the corresponding area of the lower leaf surface.

According to other embodiments, the present invention provides seeds as defined above, wherein inoculation of the plant grown from said seed with PVY results in minor or no appearance of mosaic like green spots on the leaves of said plant.

According to other embodiments, the present invention provides seeds as defined above, comprising within its genome a DNA sequence which couples with resistance to a potyvirus, and a DNA sequence which couples with susceptibility to potyvirus, wherein said pepper plant is resistant to powdery mildew.

According to other embodiments, the present invention provides seeds as defined above, wherein the DNA sequence coupling with potyvirus resistance is a template for amplification of a DNA fragment using a first primer having a polynucleotide sequence as set forth in SEQ ID NO:2 and a second primer having a polynucleotide sequence as set forth in SEQ ID NO:3, said DNA fragment lacking a restriction site for the restriction enzyme BseNI.

According to other embodiments, the present invention provides seeds as defined above, wherein the DNA sequence coupling with potyvirus susceptibility is a template for amplification of a DNA fragment using a first primer having a polynucleotide sequence as set forth in SEQ ID NO:2 and a second primer having a polynucleotide sequence as set forth in SEQ ID NO:3, said DNA fragment containing a restriction site for the restriction enzyme BseNI.

According to other embodiments, the present invention provides a pepper plant, or a part thereof, produced by growing the aforementioned seed as defined above.

According to other embodiments of the present invention the pepper grown from the aforementioned seed is homozygous for the potyvirus resistance allele and for the PM resistance allele.

According to other embodiments of the present invention the pepper grown from the aforementioned seed is homozygous for the potyvirus resistance allele and heterozygous for the PM resistance allele.

According to other embodiments of the present invention the pepper grown from the aforementioned seed is selected from the group consisting of an inbred line and a hybrid.

According to other embodiments, the present invention provides the pollen of the pepper plant grown from the aforementioned seed.

According to other embodiments, the present invention provides the ovule of the plant of grown from the aforementioned seed.

According to other embodiments, the present invention provides a fruit of a pepper plant comprising within its genome at least one potyvirus resistance allele and at least one powdery mildew (PM) resistance allele, present in cis position on the same chromosome such that the two resistance alleles are co-inherited, wherein the fruit is edible sweet fruit.

According to other embodiments, the present invention provides the fruit as defined above, wherein the potyvirus is selected from the group consisting of potato virus Y (PVY), potato virus A (PVA), tobacco etch virus (TEV) and pepper mottle virus (PepMoV).

According to other embodiments, the present invention provides the fruit as defined above, wherein the potyvirus is PVY.

According to other embodiments, the present invention provides a tissue culture of regenerable cells or protoplasts obtained from the pepper plant as defined above, or a part thereof.

According to other embodiments, the present invention provides the tissue culture as defined above, wherein the regenerable cells or protoplast of said tissue culture are obtained from a plant part selected from the group consisting of leaves, pollen, embryos, roots, root tips, anthers, flowers, fruit and seeds.

According to other embodiments, the present invention provides the tissue cultures defined above, wherein said tissue culture regenerates a plant comprising within its genome at least one potyvirus resistance allele and at least one powdery mildew (PM) resistance allele, present in cis configuration on the same chromosome such that the two resistance alleles are in coupling phase.

According to yet further embodiments, the present invention provides pepper plants, wherein the plants or progeny or parts thereof have been transformed so that their genetic material contain one or more transgenes operably linked to one or more regulatory elements. Pepper plants and parts thereof produced from the transformed plants are also encompassed within the scope of the present invention. According to one embodiment, the transformed gene or genes confer a characteristic selected from the group consisting of herbicide resistance, insect resistance, resistance to bacterial, fungal or viral disease, male sterility and vigorous growth. Nevertheless, according to other currently preferred embodiments, the pepper plants of the present invention are not genetically modified.

Methods of Generating the Pepper Plants of the Present Invention

According to another aspect, the present invention provides a method of producing a pepper plant comprising within its genome at least one potyvirus resistance allele and at least one powdery mildew (PM) resistance allele wherein the alleles are present in cis configuration on the same chromosome, comprising the steps of:

a) providing a first pepper plant resistant to infection by *L. taurica* and susceptible to potato virus Y (PVY) and a second pepper plant susceptible to infection by *L. taurica* and resistant to PVY;

b) crossing the first and the second pepper plants of step (a) to produce an F1 pepper plant progeny;

c) selfing the F1 pepper plant of step (b) to produce an F2 pepper plant progeny;

d) analyzing the progeny of step (c) for plants resistant to infection with *L. taurica* comprising within their genome a PVY resistant allele and a PVY susceptibility allele; and e) selecting at least one plant having the characteristics of step (d), comprising within its genome at least one potyvirus resistance allele and at least one powdery mildew (PM) resistance allele wherein the alleles are present in cis configuration on the same chromosome.

According to certain embodiments, the method further comprises selfing the plant of step (e) to obtain a progeny homozygous for the potyvirus resistance allele and the PM resistance allele.

According to further embodiments, the method as defined above further comprises the steps of:

a) isolating a genomic DNA sample from the F2 plant;
b) amplifying a DNA segment using a first primer having a polynucleotide sequence as set forth in SEQ ID NO:2 and a second primer having a polynucleotide sequence as set forth in SEQ ID NO:3; and,
c) subjecting the amplified DNA segment to restriction with the restriction enzyme BseNI;

wherein the absence of a BseNI restriction site within said amplified DNA segment characterizes the plant as resistant to infection by potyvirus and the presence of the BseNI site characterizes the plant as susceptible to infection by potyvirus.

Pepper plant resistant to infection by *L. taurica* and susceptible to potato virus Y (PVY) and pepper plant susceptible to infection by *L. taurica* and resistant to PVY can be identified by infecting candidate plants with the pathogen and examining the disease symptoms or by using molecular markers, as described hereinabove.

The plants provided in step (a) may be wild type or cultivated plants, or modified plants such as mutagenized or transformed plants. The progeny analyzed in step (d) from which the desired plants are selected is preferably an F2 generation; however, the desired recombinant plants can be of any generation, including F2, F3, etc. generation; backcross (BC1, BC2 etc.) generation; etc. The progeny analyzed depends on the crossing/selection scheme desired and the alleles present in the plants used. Molecular assays and/or inoculation assays may be performed in different generations; thus steps (a)-(d) may be repeated several times, in order to identify recombinants comprising the desired PM-resistance and potyvirus-resistance alleles at a cis configuration on the same chromosome.

The selection of a recombinant plant comprising a PM and a potyvirus resistance allele in the cis configuration and the introgression of this single Mendelian unit into other plants may be achieved using a combination of molecular biology, plant pathology and traditional breeding techniques. In a preferred approach, the present invention uses molecular biology techniques to discriminate between different alleles at the PM and pvr loci to combine the desirable alleles for powdery mildew resistance and potyvirus, specifically PVY resistance into the genome of cultivated pepper. The present invention facilitates the breeding of pepper hybrids with dual resistance to PM and potyviruses and provides the means to combine the PM and potyvirus resistance with other desired traits, including resistance to additional diseases.

The present invention also encompasses plants produced by the method of the present invention, parts thereof, tissue cultures derived therefrom and seeds produced by same.

The present invention discloses for the first time that resistance to potyvirus, specifically resistance to PVY, is in a tight linkage with susceptibility to infection by the fungus *L. taurica* which causes the powdery mildew disease in various plant species, including pepper plants. Therefore, it is now disclosed that surprisingly, resistance to potyvirus infection in pepper plants is in repulsion phase linkage with the resistance to powdery mildew disease.

Accordingly, the present invention now discloses that it is possible to use the genetic markers hitherto known to distinguish between potyvirus-resistant and susceptible plants, in order to allocate plants resistant to infection by *L. taurica*.

Thus, according to a further aspect, the present invention provides a method for characterizing a pepper plant as resistant or susceptible to infection by *L. taurica*, comprising the steps of:

a) isolating a genomic DNA sample from the plant;

b) analyzing the DNA sample for the presence of a DNA segment comprising a polynucleotide having the nucleic acid sequence as set forth in SEQ ID NO:1 or a fragment thereof; and c) subjecting the amplified DNA segment to restriction with the restriction enzyme BseNI;

wherein the presence BseNI restriction site within said amplified DNA segment characterizes the plant as resistant to infection by *L. taurica* and the absence of the BseNI characterizes the plant as susceptible to infection by *L. taurica*. The above is a surprisingly convenient method for screening and selecting for powdery mildew resistant pepper plants.

The following examples are presented in order to more fully illustrate certain embodiments of the invention. They should in no way, however, be construed as limiting the broad scope of the invention. One skilled in the art can readily devise many variations and modifications of the principles disclosed herein without departing from the spirit and scope of the invention.

DEPOSIT INFORMATION

A sample of an exemplary pepper line of the present invention has been deposited with the National Collections of Industrial, Food and Marine Bacteria (NCIMB), 23 St Machar Drive, Aberdeen, Scotland, AB24 3RY, United Kingdom. This exemplary pepper line is designated as 'MGR13F01-2281/1WH'.

To satisfy the enablement requirements of 35 U.S.C. 112, and to certify that the deposit of the present invention meets the criteria set forth in 37 CFR 1.801-1.809 and Manual of Patent Examining Procedure (MPEP) 2402-2411.05, Applicants hereby make the following statements regarding the deposited exemplary line 'MGR13F01-2281/1WH' (deposited as NCIMB Accession No. 42165 on Sep. 25, 2013):

The deposit is made under the terms of the Budapest Treaty, the instant invention will be irrevocably and without restriction released to the public upon the granting of a patent. Applicant(s) provides assurance of compliance by following statements:

1. During the pendency of this application, access to the invention will be afforded to the Commissioner upon request;

2. All restrictions on availability to the public will be irrevocably removed upon granting of the patent under conditions specified in 37 CFR 1.808;

3. The deposit will be maintained in a public repository for a period of 30 years or 5 years after the last request or for the effective life of the patent, whichever is longer;

4. A test of the viability of the biological material at the time of deposit will be conducted by the public depository under 37 CFR 1.807; and 5. The deposit will be replaced if it should ever become unavailable.

Access to this deposit will be available during the pendency of this application to persons determined by the Commissioner of Patents and Trademarks to be entitled thereto under 37 C.F.R. §1.14 and 35 U.S.C. §122. Upon granting of any claims in this application, all restrictions on the availability to the public of the variety will be irrevocably removed by affording access to a deposit of at least 2,500 seeds of the same variety with the NCIMB.

EXAMPLES

Example 1

Evaluation of Resistance Using Biological Assays

1. Evaluation of Resistance to Infection by the Fungus *L. taurica.*

Powdery mildew disease is caused by the fungus *Leveillula taurica*. This fungus is an obligatory parasite, i.e. it can propagate only on living plants. The fungus infects the plant leaves only. Typically, the older (lower) leaves of the plant are infected first, and then the fungus spread to the upper part of the plant to young leaves. Examination of plants for susceptibility/resistance to *L. taurica* was performed according to the procedure described below.

Inoculum's Preparation

As indicated above, the fungus *L. taurica* must be propagated on a living plant material. Thus, an inuculm is kept by infecting susceptible pepper plants in a two-week cycle. In each cycle, 10-20 containers of 1-liter each containing one susceptible pepper seedling (Hazera Genetic internal varieties T-52, L-3 and L-4) are inoculated with spores from infected leaves by air-dispersion. The containers with the infected plants are kept in a semi-controlled environment in which the temperature was kept below 32° C. Three subsequent cycles are kept to ensure sufficient amount of inoculum.

Inoculation of Examined Plants

Seeds from lines obtained during the breeding program are seeded in Hishtil® trays (Hishtil, Israel) containing peat and vermiculite. About 20-70 seeds of each examined line are seeded, of which about 10-50 plants are inoculated. The trays are kept at semi-controlled environment at a temperature between 17° C. to 42° C.

Just before inoculations the seedling are transferred from the trays to 1-liter containers. Inoculation takes place about 30-35 days after seeding, when the seedlings have 4-5 true leaves.

Evaluation of Plant Response

Typical symptoms of powdery mildew appear about 12-14 days after inoculation. Symptoms (which appear on susceptible plants only) include chlorotic spots on the upper leaf surface and a white powder-like sporulation on the corresponding area of the lower leaf surface. Plant response is typically evaluated about 19-23 days after inoculation, although the specific time may vary according to the rate of symptom development. In each experiment, plants with known genotypes (i.e. resistant/susceptible plants) are used as a control. Examined plants are evaluated only when the control plants show the expected response.

A plant is defined as susceptible when a massive sporulation accompanied with fast distribution of chlorotic spots is observed.

A plant is defined as resistant if no sporulation and/or chlorosis are observed.

A plant is defined as partially resistant if only local, small clusters of sporulation appear on the lower leaf surface and there is a low number of very small chlorotic spots. FIG. 1 shows the lower leaf surface of leaves obtained from resistant pepper plants (right hand side) and susceptible plants (left hand side). As shown, the leaves obtained form the susceptible pepper plant express the typical symptoms of powdery mildew infection as defined above, while the resistant leaves have the appearance of uninfected leaves.

2. Evaluation of Resistance to Infection by Potato Virus Y (PVY).

In nature, symptoms of infection with PVY include shortening of the stem internodes, leaf spotting in a mosaic-like pattern, severe malformation of the upper leaves, defoliation, and early plant death. For the purpose of resistance evaluation, only the leaves are examined for the appearance of malformation and mosaic like dark green spots. Evaluation was performed according to the procedure described below.

Inoculum's Preparation

Pepper plants infected with PVY are constantly kept in a greenhouse, at a temperature of between 18° C. to 25° C., with additional light period of 8 hours (from 16:00 to 22:00) provided by mercury lamps (all year long). Inoculum is prepared by grinding infected plant material in tap water at a plant material:tap water ratio of 1:150 (typically, one (1) gram of infected plant material is ground in 150 ml of tap water). The obtained mixture is used for inoculation.

Inoculation of Examined Plants

Seeds from lines obtained during the breeding program are seeded in Hishtil® trays (Hishtil, Israel). For each examined line, about 30-60 plants are inoculated by spreading the inoculum mixture obtained as described above on the plant leaves. Inoculation takes place about 30-35 days after seeding, when the seedlings have 4-5 true leaves. Susceptible pepper plant lines (Hazera L4, 1195) and tobacco plants are used as a positive control for the success of inoculation assay.

Evaluation of Plant Response

Typical symptoms of PVY infection appear about 3-4 weeks after inoculation. Susceptible plants show slight leaf malformation and a mosaic-like pattern of dark green spots. Resistant plants show no symptoms.

Example 2

Evaluation of Resistance Using Genetic Tools

DNA Isolation

Solutions:

Extraction Buffer:

| | |
|---|---|
| Sorbitol | 0.35M |
| Tris-base | 0.1M |
| EDTA | 5 mM | pH adjusted to 7.5 with concentrated HCl.

Nuclear Lysis Buffer:

10 ml of 0.5M EDTA pH 8.0

40 ml of 5.0M NaCl 2 gr CTAB

The solution is stirred overnight and the pH is adjusted to 7.5 with concentrated HCl. The solution is then diluted with distilled water to total volume of 90 ml.

Sarcosyl Solution:

5% N-lauroylsarcosine

TE Solution 10 mM Tris-HCl pH 8.0

1 mM EDTA

Storage Buffer 80 ml of 95% Ethanol 20 ml of 1M Na-acetate pH is adjusted to 7.5 with concentrated HCl.

Octanol/Chloroform Solution (1:24)

One volume of octanol is mixed with 24 volumes of chloroform.

DNA Extraction Procedure

Total DNA was extracted from fresh plant tissue (leaf, green fruit, seedlings) using the following procedure:

1. Fresh extraction solution is prepared by mixing 20 ml of Extraction Buffer, 20 ml of Nuclear Lysis Buffer and 8 ml of Sarcosyl solution. 0.38 mg of Sodium bi-sulfate is added and well mixed with the solution.
2. About 3 gr of fresh young plant tissue are grinded with a small amount of sand (Sigma 59887) and 1 ml of extraction solution. 1 ml of the mixture is transferred to 1.5 ml microcentrifuge tube and incubated for 15 min at 65° C.
3. 600 µl of octanol:chloroform (1:24) solution is then added to the mixture of step 2, mixed by vortex and centrifuged for 5 min (12000 rpm).

4. The upper phase obtained after centrifugation is transferred to a new tube, without disturbing the cell-debris pellet.
5. 600 μl of isopropanol is added and the solution is mixed gently by inverting the tube until precipitates are formed.
6. The samples are centrifuged for 5 min (12000 rpm).
7. The upper phase is discarded, 500 μl of storage buffer is added and the centrifugation (step 6) is repeated.
8. The upper phase is discarded again and the pellet is dried in a SpeedVac machine.
9. DNA pellet is eluted with 60 μl TE solution and incubated for 15 min at 65° C.
10. The DNA can be stored at 4° C. for a short period or at the freezer for a long period of storage.

Molecular Markers

Selection of plants resistant to powdery mildew and/or PVY was also based on the allelic configuration of the examined plants. Plants that are homozygous recessive to the pvr1 allele are resistant to PVY. In nature, these plants are susceptible to powdery mildew. Reference is now made to FIG. 3 presenting SEQ. ID NO:1, which is the nucleotide sequence of a DNA fragment amplified from the pvr1 gene. Specific primers, which are underlined in the aforementioned FIG. 3, were designed to amplify the DNA segment of about 700 by from within the pvr1 gene, which is indicative of the alleles present in the genome of the examined plant: when this DNA segment includes a restriction site for the restriction enzyme BseNI having the sequence ACTGGn (SEQ. ID NO:4) it is indicative of the presence of the dominant susceptibility allele. Subjecting the DNA segment to this restriction enzyme, results in DNA cleavage into two fragments, one of about 130 bp and the other of about 580 bp. When the restriction site is not present within the DNA segment, it is indicative of the presence of the recessive resistance allele. The molecular assay therefore comprises isolating DNA from the examined plant; amplifying a DNA segment with specific primers; subjecting the amplified DNA segment to restriction with the restriction enzyme BseNI and analyzing the restriction products.

DNA was isolated from examined plants by the method described hereinabove. A DNA segment was amplified by PCR reaction using the following primers:

```
Forward:
5' TGAGGCAGATGATGAAGTTGA 3'    (SEQ ID NO: 2)

Reverse:
5' CAACCATAAATATACCCCGAG 3'    (SEQ ID NO: 3)
```

PCR was carried out in a 25 μl volume containing 50 ng genomic DNA, 50 mM KCl, 10 mM Tris-HCl, 2 mM MgCl2, 0.2 mM each dNTP, 0.4 μM each forward primer and reverse primer, and 1 unit Taq polymerase (Fermentas). PCR was performed using an MJ research thermocycler model PTC-100 (MJ Research, Ramsey, Minn., USA). Cycling conditions were 95° C. 3 min; 35 cycles of (95° C. 1 min, 60° C. 1 min, 72° C. 1 min) and 72° C. 7 min.

After completion of the PCR reaction, the amplified DNA was subjected to restriction by the restriction enzyme BseNI. Aliquots of 20 μl PCR product were digested with 5 units of the BseNI restriction endonuclease and 2.5 μl, 10·X reaction buffer provided by the manufacturer (total volume 25 μl) for 3 h at 65° C. (the temperature recommended by the manufacturer).

The restriction products were analyzed by gel electrophoresis. 20 μl of the reaction products were loaded on 2% agarose gel in 1×TAE buffer and run for 3 hours.

Figure 2:
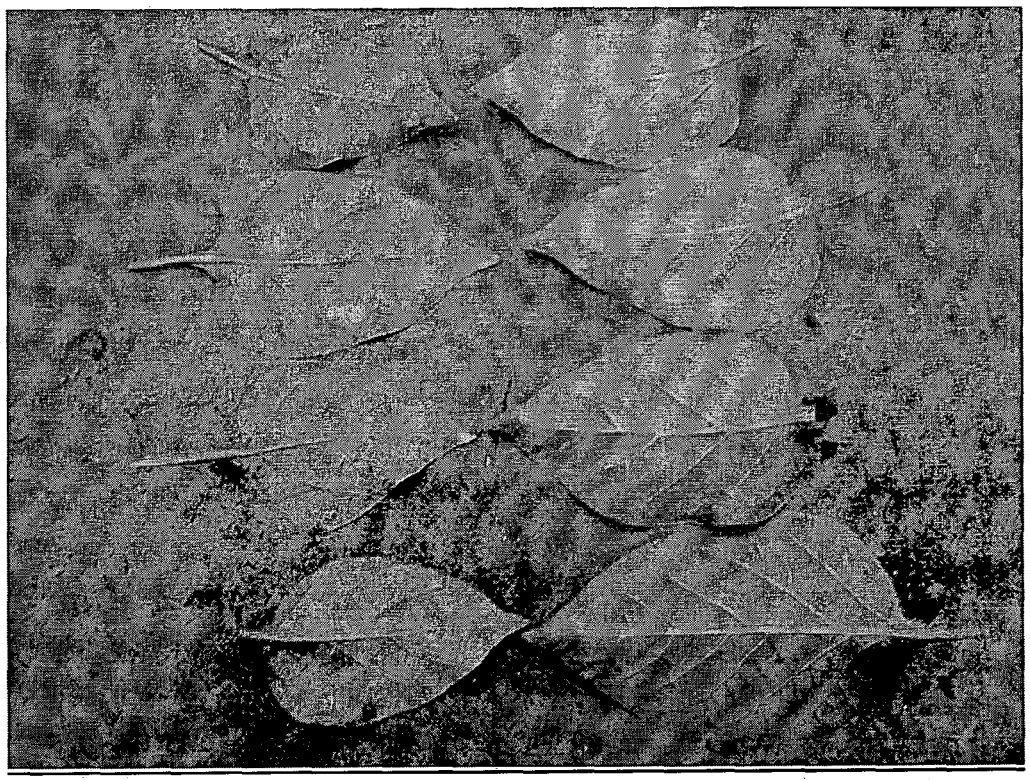

Reference is now made to FIG. 2 showing the segregation of the pvr gene in F2 plants. The presence of only one DNA segment in a length of 711 by having a nucleic acid sequence as set forth in SEQ ID NO:1 (FIG. 3) is indicative of a plant homozygous to the PVY resistance allele (R). In wild type plants, it will also indicate that the plant is homozygous to the PM-susceptibility allele. Presence of two DNA segments, one band of a length of about 130 by (not shown) and the other band of a length of about 580 by is indicative of a plant homozygous to the PVY susceptibility allele (S). In wild type plants, it will also indicate that the plant is homozygous to the PM-resistance allele. Presence of all three DNA segments (in the length of 711 bp, 580 bp and 130 bp) is indicative of a heterozygous plant (H).

Example 3

Production of Pepper Plants Having PM Resistance Allele and PVY Resistance Allele in Cis Configuration on the Same Chromosome The source material included: pepper inbred line 50-0259A-4 that is resistant to powdery mildew (PM) and susceptible to PVY; and pepper inbred line 100/201C that is susceptible to PM and resistant to PVY. These inbred lines were crossed to produce $F_2$ population. The $F_2$ population (122 plants) plus the resistant and susceptible parents and $F_1$ progeny were planted in a greenhouse in The Volcani Center (Bet Dagan, Israel) during the winter of 2005/06. Plants were identified as resistant or susceptible to PM infection by *L. taurica* as described hereinabove. Infection and pathology evaluation was carried out twice at the stage of mature ripe fruit. The resistant parent, homozygous for PM-resistance allele did not develop any symptoms, the susceptible parent had high occurrence of fungus while plants of $F_1$ progeny were moderately resistant with low level of fungal occurrence. Based on the phenotype of the parents and $F_1$ progeny it was concluded that the resistance is inherited as partially dominant.

In the $F_2$ population, 19 plants with no symptoms were classified as highly resistant to powdery mildew, 55 plants with low occurrence of fungus on the leaf were classified as moderately resistant and 48 plants with high occurrence of fungus on the leaf were determined to be susceptible to PM. Based on segregation of a single gene it is expected that 25% of the $F_2$ plants will be susceptible. In the $F_2$ population described above a significantly higher percentage (39%) of the plants were shown to be susceptible at a level similar to that observed for the susceptible parent. Similar results were obtained in a second $F_2$ population from the same parents. These second $F_2$ plants were inoculated by blowing the fungi from an inoculated leaf to an adjacent non inoculated leaf by in Hazera Greenhouse (Mivhor, Israel) in March 2006. The deviation from expected Mendelian segregation ratios is a well know phenomena that may occur in specific regions of the genome in specific crosses.

DNA extracted from the $F_2$ plants was analyzed by PCR for the pvr1 resistance locus as described above. The F2 plants were also examined for their resistance to PM by the inoculation test described above. The segregation results of both PM and pvr1 showed that the 2 genes are located 2cM apart from each other. Because naturally, resistance to PM is in trans with resistance to PVY (the resistant allele to PM is on the same chromosome with the susceptible allele to PVY), a recombination event between the 2 resistant genes must occur in order to obtain plants that are resistant to both PM and PVY.

For this purpose $F_3$ plants from 5 recombinant $F_2$ plants are planted. These recombinant $F_2$ plants are homozygous resistant for one gene (PM or PVY) and heterozygous to the second gene Preferably, the biological marker pattern of the F2 plant is as of a heterozygous plant for the PVY resistance, i.e. comprises one segment of 711 bp, one segment of 580 by and one segment of 130 bp; however, the plant is substantially resistant to powdery mildew, as is confirmed by the biological assay for PM resistance. From the F3 progeny, plants comprising at least one PM resistance allele and at least one PVY resistance allele in cis configuration on the same chromosome are selected. The selection is based on the biological assay for resistance as well as on the molecular assays described above. Table 1 summarizes the results of the phenotypic and molecular assays for one F3 recombinant line (Rec-1), as an example. Twenty three plants were analysed for their PVY resistance by molecular assay as well as for the PM resistance by a biological assay.

As shown in Table 1, the plants were homozygous for the pvr resistance allele (R) and were substantially resistant to PM (R). Only two plants were partially resistant to PM (H) or were heterozygous for the PVR resistant molecular marker (H).

TABLE 1

Phenotypic and molecular assays results for F3 recombinant plants

| PM biological assay | pvr molecular assay | |
|---|---|---|
| R | R | Rec-1-1 |
| R | R | Rec-1-2 |
| H | R | Rec-1-3 |
| R | R | Rec-1-4 |
| R | R | Rec-1-5 |
| R | R | Rec-1-6 |
| R | R | Rec-1-7 |
| R | R | Rec-1-8 |
| R | R | Rec-1-9 |
| R | R | Rec-1-10 |
| R | R | Rec-1-11 |
| R | R | Rec-1-12 |
| R | R | Rec-1-13 |
| R | R | Rec-1-14 |
| R | R | Rec-1-15 |
| R | R | Rec-1-16 |
| R | R | Rec-1-17 |
| R | R | Rec-1-18 |
| R | R | Rec-1-19 |
| R | R | Rec-1-20 |
| R | H | Rec-1-21 |
| R | R | Rec-1-22 |
| R | R | Rec-1-23 |
| 21 | | Total Resistant Plants |
| 2 | | Heterozygous |

Thus by the specific breeding and selection methods of the present invention, as desired, recombinant F3 pepper plants, resistant to powdery mildew and to infection by PVY are produced as desired. These plants, homozygous for the pvr resistance allele and for the PM resistance allele, display stable co-segregation of both resistant traits.

Plants having two chromosomes of a chromosome pair carrying the resistance to PM and PVY in cis configuration are also resistant to PVY, as is confirmed by the biological assay for PVY resistance.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

REFERENCES

US Patent Documents

U.S. Pat. No. 6,350,933
U.S. Pat. No. 6,677,510
U.S. Pat. No. 5,589,612
U.S. Pat. No. 5,939,603
U.S. Pat. No. 5,986,175
U.S. Pat. No. 6,806,400

Other Publications

Daubèze et al., 1995. Plant Breed. 114:327-332.
Murphy and Deshpande, 1997. Vegetable Sci. 24:127-131.
Lefebvre et al., 2003. Theor. Appl. Genet. 107:661-666.
Kang et al. Annu. Rev. Phytopathol. 43:581-621.
Ruffel et al., 2002. The Plant J. 32:1067-1075.
Kang et al., 2005. The Plant J. 42:392-405.
Yeam et al. 2005. Theor. Appl. Genet. 112:178-186.
Akopyanz et al., 1992. Nucleic Acid Research 20:6221-6225.
Konieczny and Ausubel, 1993. The Plant J. 4:403-410.

The invention claimed is:

1. A pepper plant comprising within its genome at least one potyvirus resistance allele and at least one powdery mildew (PM) resistance allele, wherein said resistance alleles are present in cis configuration on chromosome 4, such that said two resistance alleles are in coupling phase, and wherein the potyvirus resistance allele is the pvr1 gene resistance allele, and the PM resistance allele is linked with a molecular marker lacking a BseNI restriction site when amplified by SEQ ID NO:2 and SEQ ID NO:3.

2. The pepper plant of claim 1, wherein the plant is selected from the group consisting of an inbred line and a hybrid.

3. The pepper plant of claim 1, wherein said pepper plant is substantially resistant to PM disease caused by the fungus *L. taurica* or infection by at least one potyvirus, said potyvirus selected from the group consisting of potato virus Y (PVY), potato virus A (PVA), tobacco etch virus (TEV) and pepper mottle virus (PepMoV) or both said PM disease and said at least one potyvirus.

4. The pepper plant of claim 3, wherein inoculation with *L. taurica* results in minor appearance or no appearance of powdery mildew disease symptoms on the leaves of said plant, said symptoms include chlorotic spots on the upper leaf surface and white powder-like sporulation on the corresponding area of the lower leaf surface, further wherein inoculation with PVY results in minor or no appearance of mosaic like green spots on the leaves of said plant.

5. The pepper plant of claim 1, comprising within its genome a DNA sequence which couples with resistance to a potyvirus, and a DNA sequence which couples with susceptibility to potyvirus, wherein said pepper plant is resistant to powdery mildew.

6. The pepper plant of claim 5, wherein said DNA sequence coupling with potyvirus resistance is a template for amplification of a DNA fragment using a first primer having a polynucleotide sequence as set forth in SEQ ID NO:2 and a second primer having a polynucleotide sequence as set forth in SEQ ID NO:3, said DNA fragment lacking a restriction site for the restriction enzyme BseNI, further wherein the DNA sequence coupling with potyvirus susceptibility is a template for amplification of a DNA fragment using a first primer having a polynucleotide sequence as set forth in SEQ ID NO:2 and a second primer having a polynucleotide sequence as set forth in SEQ ID NO:3, said DNA fragment containing a restriction site for the restriction enzyme BseNI.

7. A pollen, ovule or fruit of the pepper plant of claim 1, wherein the pollen, ovule or fruit comprises within its genome at least one potyvirus resistance allele and at least one powdery mildew (PM) resistance allele, wherein said resistance alleles are present in cis configuration on chromosome 4, such that said two resistance alleles are in coupling phase, and wherein the potyvirus resistance allele is the pvr1 gene resistance allele, and the PM resistance allele is linked with a molecular marker lacking a BseNI restriction site when amplified by SEQ ID NO:2 and SEQ ID NO:3.

8. The plant of claim 1, further comprising at least one additional trait selected from the group consisting of high germination rate, herbicide resistance, insect resistance, resistance to at least one disease, resistance to various types of non-biotic stress, male sterility and vigorous growth, said additional trait introduced by a method selected from the group consisting of breeding, single trait conversion and transformation.

9. A seed of a pepper plant of claim 1, wherein a plant grown from said seed comprises within its genome at least one potyvirus resistance allele and at least one powdery mildew (PM) resistance allele, wherein said resistance alleles are present in cis configuration on chromosome 4, such that said two resistance alleles are in coupling phase, and wherein the potyvirus resistance allele is the pvr1 gene resistance allele, and the PM resistance allele is linked with a molecular marker lacking a BseNI restriction site when amplified by SEQ ID NO:2 and SEQ ID NO:3.

10. The seed of claim 9, wherein the plant grown from said seed is substantially resistant to PM disease caused by the fungus *L. taurica*, or infection by at least one potyvirus, said potyvirus selected from the group consisting of potato virus Y (PVY), potato virus A (PVA), tobacco etch virus (TEV) and pepper mottle virus (PepMoV), or both said PM disease and said at least one potyvirus.

11. A pepper plant, or a pollen, ovule, or fruit of the pepper plant or a part thereof, produced by growing the seed of claim 9.

12. The plant of claim 11, further comprising at least one additional trait selected from the group consisting of high germination rate, herbicide resistance, insect resistance, resistance to at least one disease, resistance to various types of non-biotic stress, male sterility and vigorous growth, said additional trait introduced by a method selected from the group consisting of breeding, single trait conversion and transformation.

13. A tissue culture of regenerable cells or protoplasts obtained from the pepper plant of claim 1 or a part thereof, wherein the regenerable cells or protoplast of said tissue culture are obtained from a plant part selected from the group consisting of leaves, pollen, embryos, roots, root tips, anthers, flowers, fruit and seeds, and wherein the regenerable cell comprises within its genome at least one potyvirus resistance allele and at least one powdery mildew (PM) resistance allele, present in cis configuration on chromosome 4 such that the two resistance alleles are in coupling phase, and wherein the potyvirus resistance allele is the pvr1 gene resistance allele, and the PM resistance allele is linked with a molecular marker lacking a BseNI restriction site when amplified by SEQ ID NO:2 and SEQ ID NO:3.

14. The tissue culture of claim 13, wherein said tissue culture regenerates a plant comprising within its genome at least one potyvirus resistance allele and at least one powdery mildew (PM) resistance allele, present in cis configuration on chromosome 4 such that the two resistance alleles are in coupling phase, and wherein the potyvirus resistance allele is the pvr1 gene resistance allele, and the PM resistance allele is linked with a molecular marker lacking a BseNI restriction site when amplified by SEQ ID NO:2 and SEQ ID NO:3.

15. A method of producing a pepper plant comprising within its genome at least one potyvirus resistance allele and at least one powdery mildew (PM) resistance allele wherein the alleles are present in cis configuration on chromosome 4, and wherein the potyvirus resistance allele is the pvr1 gene resistance allele, and the PM resistance allele is linked with a molecular marker lacking a BseNI restriction site when amplified by SEQ ID NO:2 and SEQ ID NO:3, comprising the steps of:
  a. providing a first pepper plant resistant to infection by *L. taurica* and susceptible to potato virus Y (PVY) and a second pepper plant susceptible to infection by *L. taurica* and resistant to PVY; b. crossing said first and the second pepper plants of step (a) to produce an $F_1$ pepper plant progeny;
  c. selfing the $F_1$ pepper plant of step (b) to produce an $F_2$ pepper plant progeny;
  d. analyzing the progeny of step (c) for plants resistant to infection with *L. taurica* said plants comprising within their genome a PVY resistant allele and a PVY susceptibility allele on chromosome 4; and
  e. selecting at least one plant having the characteristics of step (d), comprising within it genome at least one potyvirus resistance allele and at least one powdery mildew (PM) resistance allele wherein the alleles are present in cis configuration on chromosome 4, and wherein the potyvirus resistance allele is the pvr1 gene resistance allele, and the PM resistance allele is linked with a molecular marker lacking a BseNI restriction site when amplified by SEQ ID NO:2 and SEQ ID NO:3.

16. The method of claim 15, further comprising selfing the plant of step (e) to obtain a progeny homozygous for the potyvirus resistance allele and the PM resistance allele.

17. The method of claim 15, further comprising the steps of:
  a. isolating a genomic DNA sample from said $F_2$ pepper plant;
  b. amplifying a DNA segment using a first primer having a polynucleotide sequence as set forth in SEQ ID NO:2 and a second primer having a polynucleotide sequence as set forth in SEQ ID NO:3; and
  c. subjecting the amplified DNA segment to restriction with the restriction enzyme BseNI, wherein the absence of a BseNI restriction site within said amplified DNA segment characterizes said plant as resistant to infection by potyvirus and the presence of the BseNI site characterizes said plant as susceptible to infection by potyvirus.

18. A method for characterizing a pepper plant as resistant or susceptible to infection by *L. taurica*, comprising the steps of:
   a. isolating a genomic DNA sample from the plant;
   b. amplifying a DNA segment using a first primer having a polynucleotide sequence as set forth in SEQ ID NO:2 and a second primer having a polynucleotide sequence as set forth in SEQ ID NO:3; and
   c. subjecting the amplified DNA segment to restriction with the restriction enzyme BseNI,
   wherein the presence of BseNI restriction site within said amplified DNA segment characterizes said plant as resistant to infection by *L. taurica* and the absence of the BseNI site characterizes said plant as susceptible to infection by *L. taurica*.

* * * * *

UNITED STATES PATENT AND TRADEMARK OFFICE
CERTIFICATE OF CORRECTION

PATENT NO.        : 8,642,845 B2                                           Page 1 of 1
APPLICATION NO.   : 12/866154
DATED             : February 4, 2014
INVENTOR(S)       : Paran et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 278 days.

Signed and Sealed this
Twenty-ninth Day of September, 2015

Michelle K. Lee
*Director of the United States Patent and Trademark Office*

SEQUENCE LISTING

```
<160> NUMBER OF SEQ ID NOS: 3

<210> SEQ ID NO 1
<211> LENGTH: 711
<212> TYPE: DNA
<213> ORGANISM: Capsicum annuum
<220> FEATURE:
<221> NAME/KEY: primer_bind
<222> LOCATION: (1)..(21)
<220> FEATURE:
<221> NAME/KEY: gene
<222> LOCATION: (22)..(690)
```

```
<220> FEATURE:
<221> NAME/KEY: misc_feature
<222> LOCATION: (603)..(603)
<223> OTHER INFORMATION: A, T, G, C nucleotides
<220> FEATURE:
<221> NAME/KEY: misc_feature
<222> LOCATION: (646)..(646)
<223> OTHER INFORMATION: A, T, G, C nucleotides
<220> FEATURE:
<221> NAME/KEY: primer_bind
<222> LOCATION: (691)..(711)

<400> SEQUENCE: 1
tgaggcagat gatgaagttg aagaaggtga aattgttgaa gaaactgatg atacgacgtc    60
gtatttgagc aaagaaatag caacaaagca tccattagag cattcatgga ctttctggtt   120
tgataatcca gtggcgaaat cgagacaagc tgcttggggt agctcgcttc gcaacgtcta   180
cactttctcc actgttgaag attttggggg tgcttgtaaa ttttttttaa tttaatttaa   240 ttttttttatt ttattgcttt ttttttttttg tttaataaat tgggtattag gggaatcgaa   300
caatcacgaa caaggtggaa gtttaggtag ccaattaact gagttattgc gatttttatt   360
ttagttaagt ttttttttaag gcgtaatata taaatgtgca ctttaatata cccttgaact   420
tgtataaagt tgaacaggta gacacatgtt ccttatgtag tgtcctacag gtattatgac   480
gcattgggac gttgtgtctg cttgtgcacg tccaaagttg gtcataaatg cgaattgatg   540
ccaagttaaa gggccatgtt tatgtattat gcgttttttt taagcttatt ataggggaat   600
ggnaaatggg gaggaattgc aaggtgagga atcgaccctt catgancaag gtaaaagttg   660
aggtagataa tcaattgagc tactaagatt ctcggggtat atttatggtt g            711

<210> SEQ ID NO 2
<211> LENGTH: 21
<212> TYPE: DNA
<213> ORGANISM: Capsicum annuum
<220> FEATURE:
<221> NAME/KEY: misc_feature
<222> LOCATION: (1)..(21)

<400> SEQUENCE: 2
tgaggcagat gatgaagttg a                                              21

<210> SEQ ID NO 3
<211> LENGTH: 21
<212> TYPE: DNA
<213> ORGANISM: Capsicum annuum
<220> FEATURE:
<221> NAME/KEY: misc_feature
<222> LOCATION: (1)..(21)

<400> SEQUENCE: 3
caaccataaa tatccccga g                                               21
```